US011267851B2

(12) United States Patent
Cha et al.

(10) Patent No.: US 11,267,851 B2
(45) Date of Patent: Mar. 8, 2022

(54) ANTIMICROBIAL ADHESIVE PROTEIN, ANTIMICROBIAL NANOPARTICLE, ANTIMICROBIAL COMPOSITION COMPRISING SAME NANOPARTICLE, AND PREPARATION METHOD FOR SAME COMPOSITION

(71) Applicants: POSCO, Pohang-si (KR); POSTECH ACADEMY-INDUSTRY FOUNDATION, Pohang-si (KR)

(72) Inventors: Hyung Joon Cha, Pohang-si (KR); Yun Kee Jo, Pohang-si (KR); Yeonsu Jeong, Busan (KR)

(73) Assignees: POSCO, Pohang-si (KR); POSTECH ACADEMY-INDUSTRY FOUNDATION, Pohang-si (KR)

( * ) Notice: Subject to any disclaimer, the term of this patent is extended or adjusted under 35 U.S.C. 154(b) by 0 days.

(21) Appl. No.: 16/631,133

(22) PCT Filed: Jul. 13, 2018

(86) PCT No.: PCT/KR2018/007980
§ 371 (c)(1),
(2) Date: Jan. 14, 2020

(87) PCT Pub. No.: WO2019/017658
PCT Pub. Date: Jan. 24, 2019

(65) Prior Publication Data
US 2020/0231637 A1    Jul. 23, 2020

(30) Foreign Application Priority Data

Jul. 18, 2017    (KR) .................. 10-2017-0090691

(51) Int. Cl.
*A61K 38/00*    (2006.01)
*A61K 47/54*    (2017.01)
*A61K 45/06*    (2006.01)
*A61K 9/00*    (2006.01)
*A61K 9/51*    (2006.01)
*A61K 9/14*    (2006.01)
*A61P 31/04*    (2006.01)
*C07K 7/06*    (2006.01)
*C07K 7/08*    (2006.01)
*C07K 14/435*    (2006.01)

(52) U.S. Cl.
CPC .......... *C07K 14/43504* (2013.01); *A61K 9/51* (2013.01); *A61K 47/54* (2017.08); *A61P 31/04* (2018.01); *C07K 7/06* (2013.01); *C07K 7/08* (2013.01); *A61K 38/00* (2013.01); *A61K 45/06* (2013.01)

(58) Field of Classification Search
CPC ........ A61K 38/00; A61K 45/06; A61K 47/54; A61K 9/00; A61K 9/14; A61K 9/51; A61P 31/04; C07K 14/435; C07K 14/43504; C07K 7/06; C07K 7/08

USPC .......................................................... 514/2.3
See application file for complete search history.

(56) References Cited

U.S. PATENT DOCUMENTS

| | | | |
|---|---|---|---|
| 6,294,187 B1 * | 9/2001 | Boyce ....................... | A61F 2/32 424/422 |
| 2013/0052712 A1 | 2/2013 | Cha et al. | |
| 2014/0005356 A1 | 1/2014 | Cha et al. | |
| 2016/0263136 A1 | 9/2016 | Cha et al. | |
| 2016/0376738 A1 * | 12/2016 | Kim ....................... | D04H 1/728 514/2.3 |
| 2020/0062809 A1 | 2/2020 | Lee et al. | |

FOREIGN PATENT DOCUMENTS

| | | |
|---|---|---|
| KR | 10-2014-0002244 A | 1/2014 |
| KR | 10-20140035251 A | 3/2014 |
| KR | 10-2015-0112318 A | 10/2015 |
| KR | 10-2015-0143173 A | 12/2015 |
| KR | 10-2015-0143174 A | 12/2015 |
| KR | 10-2016-0026441 A | 3/2016 |
| KR | 10-2016-0110864 A | 9/2016 |
| KR | 10-2016-0129982 A | 11/2016 |
| KR | 10-2016-0144073 A | 12/2016 |

(Continued)

OTHER PUBLICATIONS

Forooshani et al, "Recent Approaches in Designing Bioadhesive Materials Inspired by Mussel Adhesive Protein," Oct. 11, 2016, 55: 9-33. (Year: 2016).*
Bahar et al., "Antimicrobial Peptides," Pharmaceuticals, 2013, 6: 1543-1575. (Year: 2013).*
Extended European Search Report dated Jun. 17, 2020 issued in European Patent Application No. 18836021.8.

(Continued)

*Primary Examiner* — Julie Ha
(74) *Attorney, Agent, or Firm* — Morgan, Lewis & Bockius LLP (57) ABSTRACT

An antimicrobial adhesive protein, an antimicrobial nanoparticle, an antimicrobial composition comprising the same nanoparticle, and a preparation method for the same composition are described and, more particularly, an antimicrobial adhesive protein in which an antibiotic peptide is linked to a mussel adhesive protein, a mussel adhesive protein derivative of which a tyrosine residue within the antimicrobial adhesive protein is modified with a catechol derivative, an antimicrobial nanoparticle including a metal capable of forming a coordinate bond with a derivative of the mussel adhesive protein and having intrinsic antimicrobial activity, an antimicrobial composition comprising the same nanoparticle, and a preparation method for the same composition are described.

8 Claims, 7 Drawing Sheets
Specification includes a Sequence Listing.

(56) References Cited

FOREIGN PATENT DOCUMENTS

| KR | 10-2017-0017499 A | 2/2017 |
| KR | 10-2017-0030943 A | 3/2017 |
| KR | 10-2017-0071792 A | 6/2017 |
| WO | 2005/092920 A1 | 10/2005 |
| WO | 2006/107183 A1 | 10/2006 |
| WO | 2018/174307 A1 | 9/2018 |

OTHER PUBLICATIONS

International Search Report in International Patent Application No. PCT/KR2018/007980, dated Nov. 2, 2018 with full English translation.
B. J. Kim, et al., "Mussel-Inspired Protein Nanoparticles Containing Iron (III)-DOPA Complexes for pH-Responsive Drug Delivery," Angewandte Chemie, 2015, vol. 127, No. 25, pp. 7426-7430.
A. A. Bahar, et al., "Antimicrobial Peptides," Pharmaceuticals, 2013, vol. 6, No. 12, pp. 1543-1575.

* cited by examiner

SEQUENCE LISTING

```
<160> NUMBER OF SEQ ID NOS: 8

<210> SEQ ID NO 1
<211> LENGTH: 13
<212> TYPE: PRT
<213> ORGANISM: Artificial Sequence
<220> FEATURE:
<223> OTHER INFORMATION: Synthetic Sequence_A7

<400> SEQUENCE: 1

Ile Leu Lys Trp Lys Trp Lys Trp Trp Lys Trp Arg Arg
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Synthetic Sequence_Tet-20

<400> SEQUENCE: 2

Lys Arg Trp Arg Ile Arg Val Arg Val Ile Arg Lys Cys
1               5                   10

<210> SEQ ID NO 3
<211> LENGTH: 7
<212> TYPE: PRT
```

```
<213> ORGANISM: Artificial Sequence
<220> FEATURE:
<223> OTHER INFORMATION: Synthetic Seuence_minTBP

<400> SEQUENCE: 3

Arg Lys Leu Pro Asp Ala Pro
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic Seuence_MP196

<400> SEQUENCE: 4

Arg Trp Arg Trp Arg Trp
1               5

<210> SEQ ID NO 5
<211> LENGTH: 13
<212> TYPE: PRT
<213> ORGANISM: Artificial Sequence
<220> FEATURE:
<223> OTHER INFORMATION: Synthetic Seuence_PTP7

<400> SEQUENCE: 5

Phe Leu Gly Ala Leu Phe Lys Ala Leu Ser Lys Leu Leu
1               5                   10

<210> SEQ ID NO 6
<211> LENGTH: 15
<212> TYPE: PRT
<213> ORGANISM: Artificial Sequence
<220> FEATURE:
<223> OTHER INFORMATION: Synthetic Seuence_Temporin 1CEa

<400> SEQUENCE: 6

Phe Val Asp Leu Lys Lys Ile Ala Asn Ile Ile Asn Ser Ile Phe
1               5                   10                  15

<210> SEQ ID NO 7
<211> LENGTH: 29
<212> TYPE: DNA
<213> ORGANISM: Artificial Sequence
<220> FEATURE:
<223> OTHER INFORMATION: Synthetic Seuence_Forward for fp-1

<400> SEQUENCE: 7
gccatatggc tagcgctaaa ccgtcttac                                    29

<210> SEQ ID NO 8
<211> LENGTH: 71
<212> TYPE: DNA
<213> ORGANISM: Artificial Sequence
<220> FEATURE:
<223> OTHER INFORMATION: Synthetic Seuence_Reverse for A7

<400> SEQUENCE: 8
ctcgagttag cggcgccatt tccaccattt ccatttccat ttcagaatct tgtacgttgg  60
aggataagaa g                                                       71
```

ANTIMICROBIAL ADHESIVE PROTEIN, ANTIMICROBIAL NANOPARTICLE, ANTIMICROBIAL COMPOSITION COMPRISING SAME NANOPARTICLE, AND PREPARATION METHOD FOR SAME COMPOSITION

CROSS-REFERENCE OF RELATED APPLICATIONS

This application is the U.S. National Phase under 35 U.S.C. § 371 of International Patent Application No. PCT/KR2018/007980, filed on Jul. 13, 2018, which in turn claims the benefit of Korean Application No. 10-2017-0090691, filed on Jul. 18, 2017, the entire disclosures of which applications are incorporated by reference herein.

SEQUENCE LISTING SUBMISSION VIA EFS-WEB

A computer readable text file, entitled "sequencelisting.txt" created on Oct. 27, 2021 with a file size of 2,225 bytes contains the sequence listing for this application and is hereby incorporated by reference in its entirety.

TECHNICAL FIELD

The present invention relates to an antimicrobial adhesive protein, a nanoparticle using the same, an antimicrobial composition including the same nanoparticle and a preparation method for the same composition.

BACKGROUND ART

Biofilms are formed by attaching bacteria to surfaces of surgical instruments and implantable medical devices, and during this process, an immune response to a host or resistance to antimicrobial substances is acquired. In this case, problems such as failure to treat patients, prolonged treatment, and complications may arise. Various antimicrobial agents and antimicrobial strategies have been developed to prevent biofilm formation through surgical infection; however, various problems such as increased resistance to antimicrobial agents, toxicity to surrounding tissues, and a limited lifespan of antimicrobial agents are emerging.

Certain strains of pathogens infecting the human body are parasitic inside host cells and continue to proliferate while controlling metabolic activity of the host. It has been revealed that *Mycobacterium tuberculosis*, typhoid bacteria, *chlamydia* and *listeria* are representative intracellular bacteria, and *E. coli* and *Staphylococcus*, commonly known as extracellular bacteria, also invade host cells and are parasitic in the host cells. In order to inhibit the infection of these intracellular bacteria, antimicrobial agents need to reach the inside of the cell by diffusion or inclusion; however, more than two-thirds of existing antimicrobial agents have limitations, in that they show no effect on the intracellular bacteria.

Antibiotic peptides (antimicrobial peptides; AMPS) are amino acid chains produced as part of an innate immune system of living organisms in nature and generally exhibit antibiotic activity against bacteria, viruses, and fungi. In particular, the antibiotic peptides break down or puncture bacterial cell membranes, resulting in loss of intracellular materials, and react with substances in bacterial cells to inhibit synthesis of bacterial nucleic acids or proteins. Accordingly, the antibiotic peptides have drawn attention as a next generation antibacterial agent.

Meanwhile, mussels, which are marine life organisms, produce and secrete adhesive proteins to securely attach themselves to wet solid surfaces such as rocks in the ocean, and thus do not get affected by waves and a buoyancy effect of seawater. The mussel adhesive proteins are known as a powerful natural adhesive and have flexibility to bend while exhibiting a tensile strength of approximately twice that of epoxy resins compared to chemical synthetic adhesives. In addition, the mussel adhesive proteins can adhere to a variety of surfaces, including plastics, glass, metals, Teflon, and biomaterials, and even to wet surfaces in a few minutes, which still remains a problem which has not yet been solved in the field of chemical adhesive development.

To obtain 1 g of a naturally extracted adhesive material from mussels, however, about 10,000 mussels are required. Despite the excellent physical properties of mussel adhesive proteins, many restrictions apply to the industrial use of naturally extracted mussel adhesive proteins. As an alternative, studies on the production of mussel adhesive proteins using genetic recombination techniques have been conducted using Mefp (*Mytilus edulis* foot protein)-1, Mgfp (*Mytilus galloprovincialis* foot protein)-1, Mcfp (*Mytilus coruscus* foot protein)-1, Mefp-2, Mefp-3, Mgfp-3, Mgfp-5 and the like.

Meanwhile, nanoparticles, capable of invading animal cells through a phagocytosis or pinocytosis pathway, have drawn attention as a strategy for inhibiting intracellular infection. In this regard, studies on improvement of the stability of antimicrobial agents and release of selective antimicrobial agents by carrying the antimicrobial agents on nanoparticles based on materials sensitive to external stimuli, such as temperature or pH, have been reported. However, most of the studies showed that the antimicrobial effects were due to the antimicrobial agents carried by the nanoparticles, and there have been no reports on a material in which the nanoparticles themselves have antimicrobial properties.

(Non-patent document 1) KR 10-2014-0002244
(Non-patent document 2) WO 06107183A

DISCLOSURE

Technical Problem

An aspect of the present invention is to provide an antimicrobial adhesive protein having antimicrobial activity itself.

Another aspect of the present invention is to provide an antimicrobial nanoparticle having inherent antimicrobial activity.

Still another aspect of the present invention is to provide a method for preparing an antimicrobial nanoparticle having inherent antimicrobial activity.

Technical Solution

According to an aspect of the present disclosure, an antimicrobial adhesive protein, in which an antibiotic peptide is connected to a mussel adhesive protein, is provided.

It is preferable that the mussel adhesive protein be a protein selected from the group consisting of *Mytilus edulis* foot protein (Mefp)-1, Mefp-2, Mefp-3, Mefp-4, Mefp-5, *Mytilus galloprovincialis* foot protein (Mgfp)-1, Mgfp-2, Mgfp-3, Mgfp-4, Mgfp-5, *Mytilus coruscus* foot protein (Mcfp)-1, Mcfp-2, Mcfp-3, Mcfp-4, Mcfp-5, foot protein (fp)-1, fp-2, fp-3, fp-4, fp-5 and fp-6, a variant thereof, or a fusion protein to which at least one protein selected from the group is linked.

It is preferable that the antibiotic peptide be at least one peptide selected from the group consisting of an A7 peptide, a Tet-20 peptide, a minTBP peptide and an MP196 peptide.

According to another aspect, an antimicrobial nanoparticle having inherent antimicrobial activity and comprising a mussel adhesive protein derivative of which a tyrosine residue in the antimicrobial adhesive is modified to a catechol derivative, and a metal capable of coordinating with the mussel adhesive protein derivative is provided.

It is preferable that the catechol derivative be at least one selected from the group consisting of 3,4-dihydroxyphenylalanine (DOPA), DOPA o-quinone, dopamine, norepinephrine, epinephrine, epigallocatechin gallate and derivatives thereof.

It is preferable that the coordinatable metal be at least one selected from the group consisting of titanium, vanadium, chrome, manganese, iron, cobalt, nickel, zirconium, niobium, molybdenum, technetium, ruthenium, rhodium, palladium, silver, hafnium, tantalum, tungsten, rhenium, osmium, iridium, platinum and gold.

It is preferable that an antimicrobial agent is additionally loaded in the antimicrobial nanoparticle.

It is preferable that the microbial agent be at least one selected from the group consisting of penicillins, cephalosporins, β-lactams, macrolides, glycopeptides, lincosamides, quinolones, rifamycin, chloramphenicol, polymycin, trimethoprim, streptogamine, oxazolidinone, gentamicin and baccitracin.

An antimicrobial effect is achieved under a condition of pH 0.1 to pH 6.5, which is a bacterial infection environment.

According to still another aspect, a method for preparing an antimicrobial nanoparticle, comprising dissolving a mussel adhesive protein derivative of which a tyrosine residue in the antimicrobial adhesive protein of any one of claims 1 to 3 is modified to a catechol derivative in a mixed solvent of water and ethanol; preparing a spinning solution by adding a salt of a metal capable of coordinating with the mussel adhesive protein derivative; and electrospinning the spinning solution is provided.

It is preferable that the mixed solvent comprise water and ethanol in a weight ratio of 20:80 to 40:60.

It is preferable that the metal salt be added so as that a molar ratio of a metal ion and a catechol derivative is 1:3 to 1:4

It is preferable that the metal be at least one selected from the group consisting of titanium, vanadium, chrome, manganese, iron, cobalt, nickel, zirconium, niobium, molybdenum, technetium, ruthenium, rhodium, palladium, silver, hafnium, tantalum, tungsten, rhenium, osmium, iridium, platinum and gold.

According to still another aspect, an antimicrobial composition, comprising the antimicrobial nanoparticle is provided.

It is preferable that the antimicrobial nanoparticle be comprised in an amount of 1.0 μg/mL to 2 μg/mL.

Advantageous Effects

The present invention allows an antibiotic peptide to inhere in a mussel adhesive protein so that the protein can be used as a bioadhesive material exhibiting an antimicrobial effect. The mussel adhesive protein may be coated on various surfaces using excellent adhesion properties thereof regardless of types of the surfaces. By preparing the same in the form of a nanoparticle, intracellular infections can be effectively prevented. In particular, the antimicrobial nanoparticle according to the present invention, when utilized for intracellular infections, is present in an inactive form in an infected animal and thus does not have any effect thereon, while having an intrinsic antimicrobial activity of killing bacteria, that is, infected endogenous bacteria in animal cells.

BEST MODE

Hereinafter, the preferred embodiment of the present invention will be described with reference to the accompanying drawings. The present invention may, however, be embodied in many different forms and should not be construed as being limited to the embodiments set forth herein.

According to the present invention, an antimicrobial adhesive protein, an antimicrobial nanoparticle and a preparation method therefor are provided.

The antimicrobial adhesive protein provided in the present invention refers to a protein having antimicrobial activity itself and having an antibiotic peptide connected to a mussel adhesive protein.

The mussel adhesive proteins disclosed in KR10-2014-0002244 A, WO2006/107183, WO2005/092920, or the like may be used for that of the present invention. A detailed preparation process may be the same as that disclosed in WO2006/107183 and WO2005/092920.

A mussel adhesive protein, which can be applied hereto, may be a mussel-derived adhesive protein, and may preferably include a mussel adhesive protein derived from *Mytilus edulis*, *Mytilus galloprovincialis* or *Mytilus coruscus*, or a variant thereof, but is not limited thereto.

The mussel adhesive protein may include a *Mytilus edulis* foot protein (Mefp)-1, Mefp-2, Mefp-3, Mefp-4, Mefp-5, *Mytilus galloprovincialis* foot protein (Mgfp)-1, Mgfp-2, Mgfp-3, Mgfp-4, Mgfp-5, *Mytilus coruscus* foot protein (Mcfp)-1, Mcfp-2, Mcfp-3, Mcfp-4, Mcfp-5, which is derived from said mussel, or a variant thereof, and may preferably include a protein selected from the group consisting of foot protein (fp)-1, fp-2, fp-3, fp-4, fp-5 and fp-6, or a fusion protein to which at least one protein selected from the group is linked, or a variant thereof, but is not limited thereto.

Further, the mussel adhesive protein of the present invention may include all mussel adhesive proteins disclosed in WO2006/107183 and WO2005/092920. Preferably, the mussel adhesive protein may include fusion proteins such as fp-151, fp-131, fp-353, fp-153, fp-351, and the like, but is not limited thereto. In addition, the mussel adhesive protein may include a polypeptide, in which 1 to 12 or more decapeptides are linked in tandem, where the decapeptides recur about 80 times in fp-1 is, and may preferably be an fp-1 variant polypeptide in which 12 decapeptides of SEQ ID NO:2 are connected in tandem, but is not limited thereto.

The present inventors developed an fp-151, a novel mussel adhesive protein in which a structure of their previous study, in which 10 repeating amino acids of the fp-1 recur 6 times, is connected to N- and C-termini of fp-5 at a genetic level, and successfully expressed the recombinant mussel adhesive protein in *E. coli*, thereby finding feasibility of mass production thereof and significantly high industrial applicability through simple purification processes (WO2006/107183 and WO2005/092920).

For example, the mussel adhesive protein may be a protein selected from the group consisting of *Mytilus edulis* foot protein (Mefp)-1, Mefp-2, Mefp-3, Mefp-4, Mefp-5, *Mytilus galloprovincialis* foot protein (Mgfp)-1, Mgfp-2, Mgfp-3, Mgfp-4, Mgfp-5, *Mytilus coruscus* foot protein (Mcfp)-1, Mcfp-2, Mcfp-3, Mcfp-4, Mcfp-5, foot protein (fp)-1, fp-2, fp-3, fp-4, fp-5 and fp-6, a variant thereof, or a fusion protein to which at least one protein selected from the group is linked.

Meanwhile, the antibiotic peptide, which can be used in the present invention, may be at least one peptide selected from the group consisting of an A7 peptide, a Tet-20 peptide, a minTBP peptide, an MP196 peptide, a PTP7 peptide and temporin 1CEa as disclosed in Table 1, but is not limited thereto.

For example, the antibiotic peptide may be at least one peptide selected from the group consisting consist of an amino acid sequence listed in Table 1 below of SEQ ID NO: 16.

TABLE 1

| SEQ ID NO | Peptide | AA sequence |
|---|---|---|
| 16 | A7 | ILKWKWKWWKWRR |
| 17 | Tet-20 | KRWRIRVRVIRKC |

TABLE 1 -continued

| SEQ ID NO | Peptide | AA sequence |
|---|---|---|
| 18 | minTBP | RKLPDAP |
| 19 | MP196 | RWRWRW |
| 20 | PTP7 | FLGALFKALSKLL |
| 21 | Temporin 1CEa | FVDLKKIANIINSIF |

According to the present invention, an antimicrobial nanoparticle having inherent antimicrobial activity is provided, and the antimicrobial nanoparticle include a metal capable of coordinating with a derivative of a mussel adhesive protein, of which a tyrosine residue in the antimicrobial adhesive protein is modified to a catechol derivative, and a derivative of the mussel adhesive protein.

As used herein, the expression "antimicrobial activity" may include an antibiotic effect of inhibiting growth of microorganisms or strains and a bactericidal effect of removing existing microorganisms or strains.

The mussel adhesive protein of the present invention, of which the tyrosine residue is modified to a catechol derivative, may refer to a "modified mussel adhesive protein" or a "a mussel adhesive protein derivative," and a modification method is not particularly limited.

The catechol derivative is a compound containing a dihydroxyl group and is coordinatable with a metal. The catechol derivative is preferably at least one selected from the group consisting of 3,4-dihydroxyphenylalanine (DOPA), DOPA o-quinone, dopamine, norepinephrine, epinephrine, epigallocatechin gallate and derivatives thereof.

For example, the catechol derivative may have 10% to 100% of the entire tyrosine residue modified to a catechol derivative, particularly to DOPA.

The coordinatable metal is any metal coordinatable with the catechol derivative and may be a typical metal or a transition metal. For example, the metal may be at least one selected from the group consisting of titanium, vanadium, chrome, manganese, iron, cobalt, nickel, zirconium, niobium, molybdenum, technetium, ruthenium, rhodium, palladium, silver, hafnium, tantalum, tungsten, rhenium, osmium, iridium, platinum and gold. The metal is preferably an iron (III).

A salt of the metal, which can be used here, may be, for example, iron (II) chloride ($FeCl_2$), iron (III) chloride ($FeCl_3$), titanium tetrachloride ($TiCl_4$), titanium (III) chloride ($TiCl_3$), cobalt (III) chloride ($CoCl_3$), Cobalt (II) chloride ($CoCl_2$), nickel chloride ($NiCl_2$), silver chloride (AgCl), and the like, but is not limited thereto.

The catechol derivative and the metal coordinate with each other to form a metal-catechol derivative complex. Preferably, the metal-catechol derivative complex may be an Fe(III)-DOPA complex. According to an exemplary embodiment, the DOPA and the Fe(III) form a crosslink through a coordination bond. As the DOPA and the Fe(III) are already present in the human bodies and are advantageous due to excellent biocompatibility.

The DOPA is known to is known to form mono-, bis-, or tris-cross-links, while reacting with the Fe(III), depending on pH. Further, the DOPA is known to exhibit unique colors of Fe(III)-DOPA complexes depending on bonding aspects. According to an exemplary embodiment of the present invention, a reagent containing Fe(III), that is, $FeCl_3$, may be used to provide Fe(III) metals. Preferably, an $FeCl_3$ solution may be added so that a molar ratio of Fe(III) to DOPA is 1:3 or a ratio of Fe(III) is less than that.

Further, the antimicrobial nanoparticle may have an antimicrobial agent additionally loaded and may be applied as a multi-drug form by for example, carrying an antimicrobial drug. The antimicrobial drug may be penicillins such as penicillin, methicillin, oxacillin, naphcillin, ampicillin, carboxyphenicillin, amoxicillin, piperecillin, or the like; cephalosporins such as cephalosporin, cephazoline, ceftazidime, cefoperazone, cefotaxime, ceftizoxime, ceftriaxone, ceftazidime, or the like; other beta-lactams such as carbapenem, meropenem, sulbactam, clavulanate, tazobactam, or the like; aminoglycosides such as streptomycin, neomycin, gentamicin, tobramycin, amikacin, sisomicin, astromicin, isepamicin, arbekacin, or the like; macrolides such as erythromycin, clarithromycin, or the like; tetracyclines such as tetracycline, metacycline, minocycline, tigecycline, doxycycline, or the like; glycopeptides such as vancomycin, teicoplanin, or the like; lincosamides such as lincomycin, clindamycin, or the like; quinolones such as nalidixic acid, oxolinic acid, fluoroquinolone, ciprofloxacin, norfloxacin, levofloxacin, or the like; rifamycin, chloramphenicol, polymyxin, trimethoprim, streptogramin, oxazolidinone, bacitracin and mixtures thereof, but is not limited thereto.

For example, it is preferable that the antibiotic agent be at least one selected from the group consisting of penicillins, cephalosporins, β-lactams, macrolides, glycopeptides, lincosamides, quinolones, rifamycin, chloramphenicol, polymycin, trimethoprim, streptogamine, oxazolidinone, gentamicin and bacitracin.

The antimicrobial nanoparticle of the present invention has inherent antimicrobial activity, and particularly in an acidic condition, that is, at pH 0.1 to pH 6.5, preferably at pH 0.1 to pH 5, for example, at pH 4.0 to pH 5.0, the nanoparticle is dissolved, thereby exhibiting antimicrobial activity.

That is, the nanoparticle maintain the nanoparticle form in body fluids having a pH of 7.4, thereby exhibiting stable properties, whereas in an acidic environment (pH of about 6.5) formed by producing acetic acids and lactic acids, metabolites produced due to bacterial infections, the nanoparticle loses its form and may induce positive charges of an original antimicrobial adhesive protein.

Accordingly, the nanoparticle based on the antimicrobial adhesive protein MAP-cAMP is present in an inactive form and dissolved at a time point where antimicrobial activity is required, thereby establishing technology enabling expression of the antimicrobial activity. This in particular enables an application of the nanoparticle in killing infected bacteria inside cells without affecting infected host animal cells.

The nanoparticle may have an average diameter of 80 nm to 130 nm, preferably 110 nm. The nanoparticle with this size is appropriate to migrate to a target cell and can be delivered via various routes including injection, oral administration, and dermal administration, when introduced to the human body. The loaded drug may be appropriately delivered to human or other mammals having a treatment-effective disease or symptoms thereof via injection or other routes, but preferably via parenteral administration.

The term "parenteral" refers to intramuscular, intraperitoneal, intraabdominal, subcutaneous, intravenous and intraarterial. Accordingly, the nanoparticle of the present invention may representatively be formulated into an injection formulation.

The injectable nanoparticle of the present invention may be injected or inserted into a human body or other mammals' bodies via any appropriate administration route, preferably via an injection with a subcutaneous needle. For example, the nanoparticle may be administered via injection to artery, vein, urogenital organs, under the skin, muscle, under the skin, skull, pericardium, pleura, or other body cavities or available spaces. Alternately, the nanoparticle may be introduced into, for example, joint during arthroscopic surgery, urogenital organs, vas, palate, pleura, or any body cavities or available spaces via a catheter or a syringe during an operation, surgical treatment, diagnosis or interventional procedure.

The nanoparticle can be used for tuberculosis, hepatitis, typhoid fever, food poisoning, cholera, dysentery and other infectious diseases, but is not limited thereto.

Further, according to the present invention, a method for preparing an antimicrobial nanoparticle having inherent antimicrobial activity as described above.

The antimicrobial nanoparticle preparation method of the present invention includes dissolving a mussel adhesive protein derivative, of which a tyrosine residue in the antimicrobial adhesive protein of the present invention, is modified to a catechol derivative in a mixed solvent of water and ethanol; preparing a spinning solution by adding a salt of a metal capable of coordinating with the mussel adhesive protein derivative; and electrospinning the spinning solution.

The electrospinning is a technique forming a nanoparticle using electrical attraction and repulsion occurring when charging a polymer solution or a molten polymer with a predetermined voltage. According to electrospinning, nanoparticles having various diameters of several nanometers to several thousands of nanometers can be prepared with simple equipment and may be applied to a variety of substances.

Use of the water-based solvent, instead of an organic solvent, may eliminate a toxic effect of the solvent remaining during the electrospinning. In order to improve evaporation of the water-based solvent, an organic solvent may be further mixed, and preferably, 60% to 80% (v/v) of ethanol may be additionally mixed with respect to distilled water. That is, the mixed solvent includes water and ethanol mixed preferably in a weight ratio of 20:80 to 40:60, more preferably in a weight ratio of 30:70.

Meanwhile, it is preferable that a salt of the metal is added so as that a molar ratio of a metal ion and a catechol derivative is 1:3 to 1:4. The metal maybe at least one selected from the group consisting of titanium, vanadium, chrome, manganese, iron, cobalt, nickel, zirconium, niobium, molybdenum, technetium, ruthenium, rhodium, palladium, silver, hafnium, tantalum, tungsten, rhenium, osmium, iridium, platinum and gold.

Electrospinning of thus-prepared spun solution is not particularly limited, but for example, may involve discharging the spun solution using a syringe pump at a speed of 0.5 mL/h to 2 mL/h and applying a high voltage of 6 kV to 14 kV when passing through a needle having a diameter of 0.1 mm to 0.8 m to generate a nanoparticle. Thus-prepared nanoparticle may be collected on a stirred tank containing aluminum phosphate buffered saline (PBS; pH 7.4), and the like, or an aluminum foil.

Further, according to the present invention, an antimicrobial composition containing the antimicrobial nanoparticle having the inherent antimicrobial activity as describe above is provided.

The antimicrobial nanoparticle is contained preferably at a concentration of 1.0 μg/mL to 2 μg/mL, more preferably at a concentration of 1.5 μg/mL. When the concentration of the antimicrobial nanoparticle is less than 1.0 μg/mL, the antimicrobial activity may be insufficient, whereas difference in effects may not be significant compared to the concentration when the concentration exceeds 2 μg/mL, thereby making it not preferable in terms of process economy.

A strain, in which the antimicrobial nanoparticle and antimicrobial composition of the present disclosure can exhibit an antibiotic effect of inhibiting growth of microorganisms or strains and a bactericidal effect of removing existing microorganisms or strains, is not particularly limited, but may be, for example, *E. coli*, and the like.

Hereinafter, the present invention will be described in more detail with reference to specific exemplary embodiments. The following exemplary embodiments are merely examples to help understanding of the present invention, and the scope of the present invention is not limited thereto.

MODE FOR INVENTION

Examples

1. Preparation of Antimicrobial Adhesive Protein MAP-cAMP

A mussel adhesive protein fp-1 (*Mytilus* mussel foot protein type 1) variant composed of 12 times-repeated decapeptides (AKPSYPPTYK) was prepared according to a known process (see Proc. Natl. Acad. Sci. USA 2010, 107, 12850-3).

A primer of a sequence for an A7 peptide (Nan, Y H, Bang, J-K, Shin, S Y, 2009. Peptides 30: 832-838), a pseudopeptide derived from indolicidin, an antimicrobial peptide, was prepared to connect to thus-prepared mussel adhesive protein fp-1 using a polymerase chain reaction (Table 2).

TABLE 2

| SEQ ID NO | Primer | Nucleotide sequence (5' → 3') |
| --- | --- | --- |
| 20 | Forward for fp-1 | GCCATATGGCTAGCGCTAAACCGTCTTAC |
| 21 | Reverse for A7 | CTCGAGTTAGCGGCGCCATTTCCACCATT TCCATTTCCATTTCAGAATCTTGTACGTT GGAGGATAAGAAG |

A product, MAP-cAMP gene was transformed into an *E. coli* TOP10 strain using a pET-22b (+) vector containing a T7 promoter as a plasmid carrier. Further, a cloned recombinant vector was transformed back into an *E. coli* BL21 (DE3) strain to express a fusion protein.

The *E. coli* BL21 transformed into the MAP-cAMP gene was cultured in an LB liquid medium containing 50 μg/mL of ampicillin at 37° C. and 300 rpm. When optical density for 600 nm ($OD_{600}$) reached 0.4 to 0.6, 1 mM isopropyl-β-D-thiogalactopyranoside (IPTG) was added and cultured at the same conditions. Thus-cultured cell was centrifuged for 10 min under conditions of 4° C. and 18,000×g, and resuspended in an elution buffer (10 mM Tris-HCl, and 100 mM sodium phosphate, pH 8) to lyse the cell at 200 Kpsi.

To obtain cell debris from thus-obtained cell lysate, a resultant was centrifuged for 20 min under conditions of 4° C. and 18,000×g. 25% (v/v) acetic acid was used to extract a target fusion protein, and the fusion protein lastly purified was lyophilized and stored at −80° C.

Figure 1:
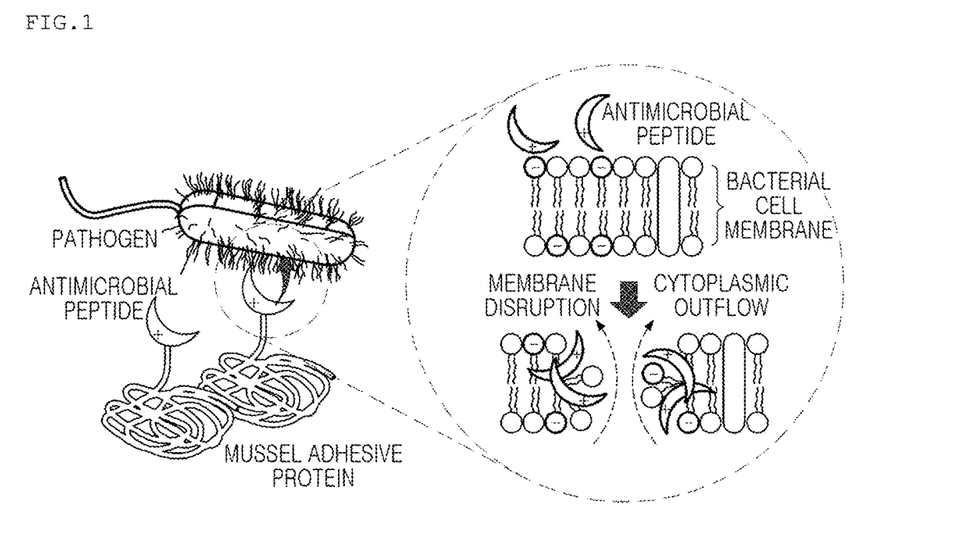
FIG. 1 is a schematic diagram illustrating the antimicrobial effect exhibited by disrupting bacterial cell membranes by actions of the antibiotic peptide on a surface on which the antimicrobial adhesive protein MAP-cAMP of the present invention is coated.
Figure 2:
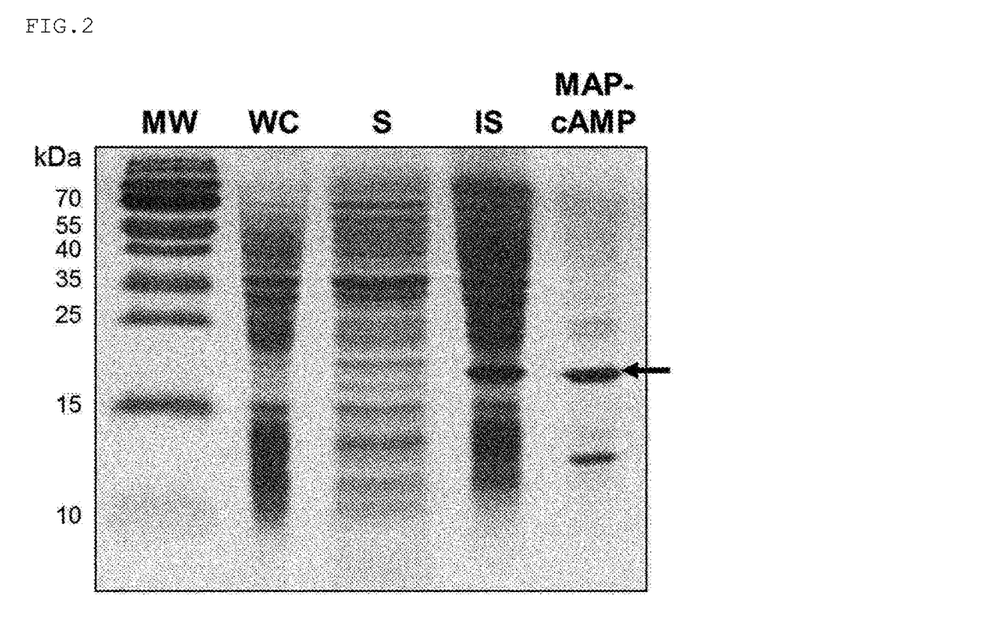
FIG. 2 illustrates a result of SDS-PAGE examining an expression of the MAP-cAMP fusion protein.
Figure 3:
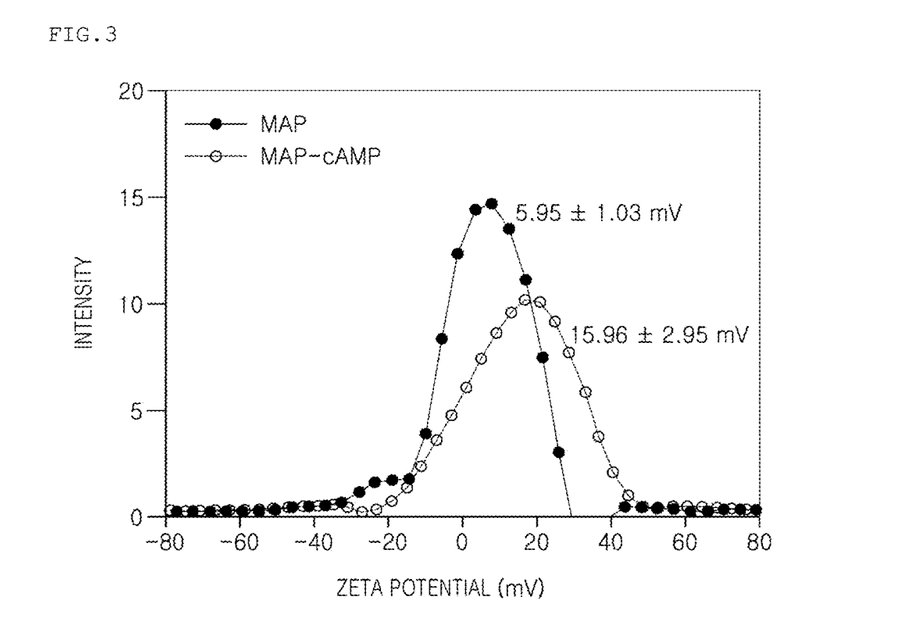
FIG. 3 illustrates a result of examining charges in a solution of the MAP-cAMP fusion protein. A MAP, in which a peptide is not fused, was used as a control.

The preparation and purification of the protein was analyzed using 12% (w/v) SDS-PAGE, and consequently confirmed successful expression of the fusion protein (FIG. 2). A concentration of the protein was measured using Bradford assay (Bio-Rad). Compared to MAP, the control protein, the prepared fusion protein MAP-cAMP exhibited a higher positive charge in a solution of pH 7.4 (FIG. 3).

2. Antimicrobial Effect of Surface Coated with Antimicrobial Surface Coating Agent To measure the antimicrobial activity of the MAP-cAMP, the antimicrobial adhesive protein prepared in 1., the protein was dissolved in distilled water at concentrations of 0 mg/mL, 5 mg/mL, 10 mg/mL and 20 mg/mL and applied to a surface in a predetermined amount so as to cover a cover slip formed of polystyrene, followed by drying for an hour at 37° C. to coat the surface. Thus-prepared MAP-cAMP-coated surface was applied to a solid medium and a liquid medium, which were inoculated with bacteria, to confirm the antimicrobial effect. An uncoated material was used as a negative control.

(1) Measurement of Antimicrobial Effect in Solid Medium

The surfaces coated with 0 mg/mL, 5 mg/mL, 10 mg/mL and 20 mg/mL MAP-cAMP as described above was cultured in an agar plate medium spread with *Escherichia coli*, a gram-negative bacterium in a log phase, at 37° C. for 1 day.

Figure 4:
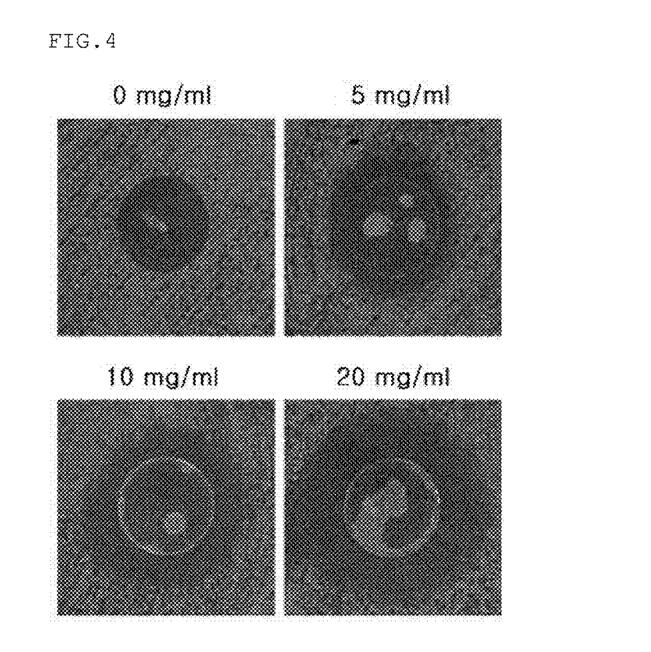
FIG. 4 illustrates a result of disk diffusion test to analyze the antimicrobial effect according to a coating concentration of the MAP-cAMP fusion protein.
Figure 5:
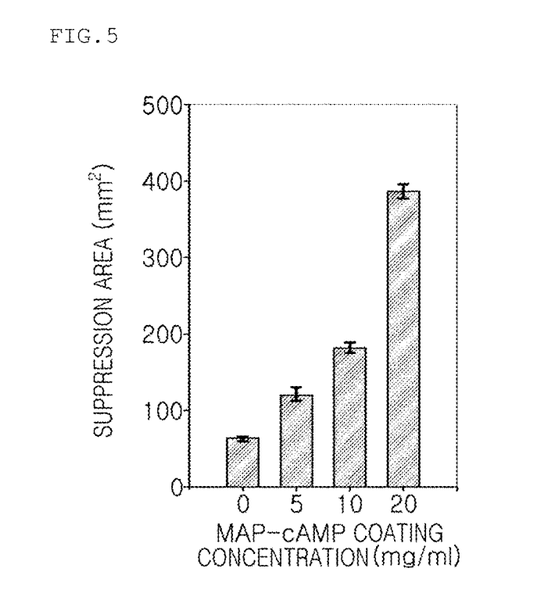
FIG. 5 is a graph schematically illustrating an inhibition area from the antimicrobial activity analysis result of FIG. 4.

The antimicrobial effect was analyzed by measuring an inhibition area using a graphic program (ImageJ). As a result, all MAP-cAMP-coated surfaces showed bacterial growth inhibition, which indicates that the higher the coating concentration, the larger the inhibition area (FIGS. 4 and 5).

(2) Measurement of Antimicrobial Effect in Liquid Medium

The cover slip formed of polystyrene used in (1) was applied to 500 μL of an LB liquid medium inoculated with *Escherichia coli*, a gram-negative bacterium in a log phase, and cultured for 24 hours to measure optical density for 600 nm ($OD_{600}$). A 48-well culture plate was used for the culturing of the bacterial strain at 37° C. and 300 rpm.

Figure 6:
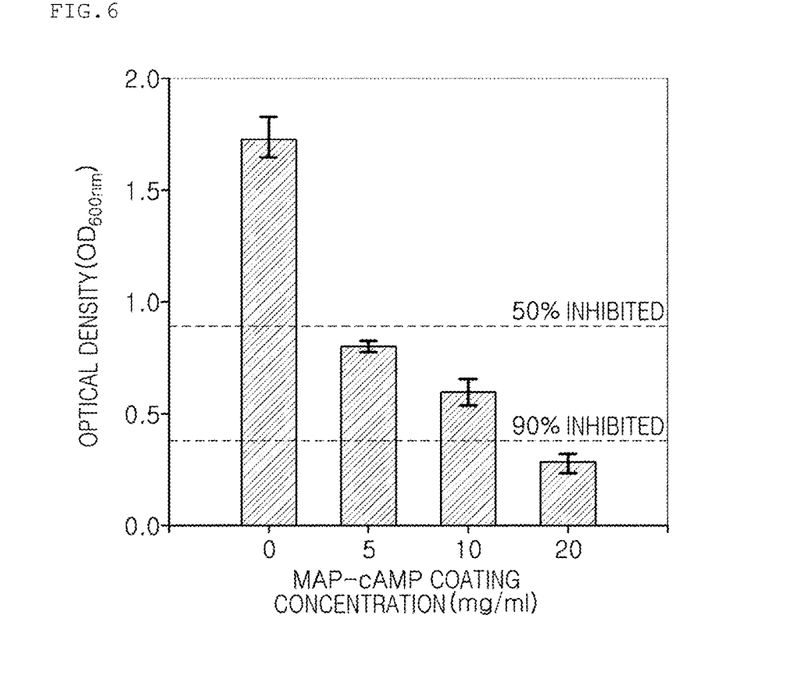
FIG. 6 is a graph illustrating optical density values 24 hours after applying a surface coated with different coating concentrations of the MAP-cAMP fusion protein to a liquid culture medium in which *E. coli* is cultured.
Figure 7:
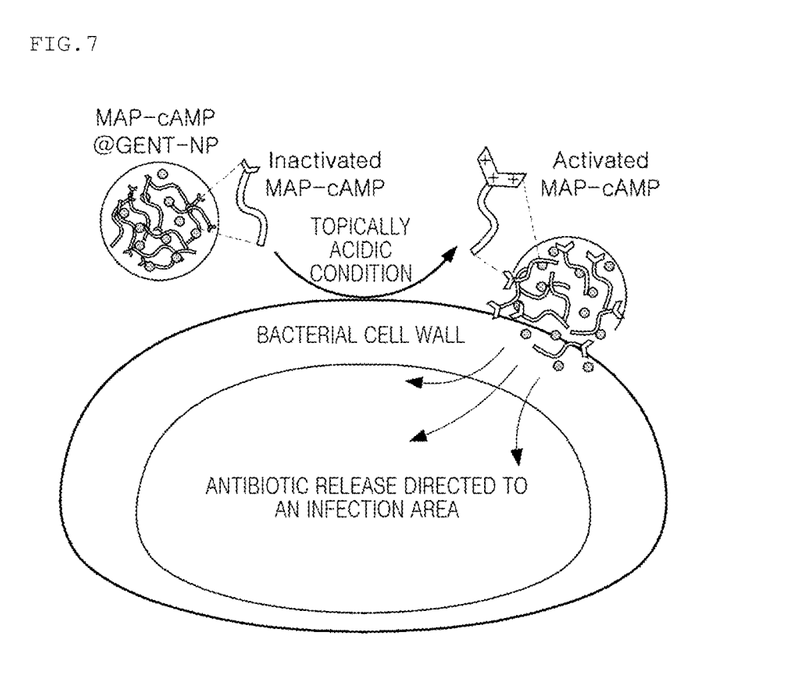
FIG. 7 is a schematic diagram illustration activation of the antimicrobial effect of a nanoparticle prepared using the antimicrobial adhesive protein MAP-cAMP in an infection environment.

As a result, a minimum coating concentration of the MAP-cAMP was shown to be 20 mg/mL for 90% inhibition of the growth of the *E. coli* and that was shown to be 5 mg/mL for 50% inhibition of the growth of the *E. coli* (FIG. 6).

3. Preparation of Antimicrobial Nanoparticle Using Fusion Protein MAP-cAMP (1) Preparation of DOPA-Modified Fusion Protein mMAP-cAMP The MAP-cAMP, the fusion protein prepared in 1, was subject to an in vitro enzymatic reaction using a mushroom tyrosinase to convert a tyrosine residue of the MAP-cAMP to dihydroxyphenylalanine (DOPA). Specifically, 1.50 mg/mL of an MAP-cAMP solution and 100 μg/mL of the tyrosinase were reacted in a buffer solution (100 mM of sodium phosphate, 20 mM of boric acid, and 25 mM of ascorbic acid; pH 6.8) for 1 hour, and dialyzed with 1% acetic acid.

(2) Preparation of Antimicrobial Nanoparticle

Figure 8:
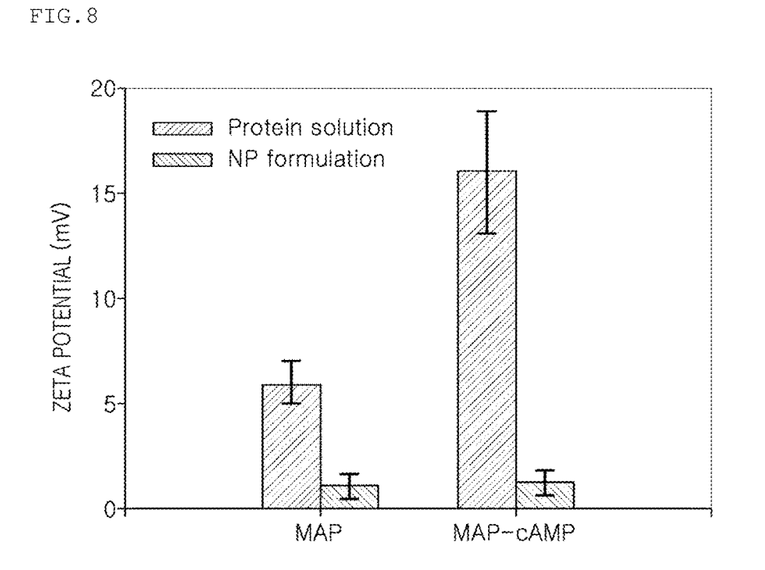
FIG. 8 illustrates a result of measuring charges of the MAP-cAMP fusion protein and the control MAP protein in the nanoparticle phase and the protein solution phase.

Electrospinning was used to prepare a nanoparticle using the mMAP-cAMP prepared in (1). Specifically, 1.5 wt % to 3 wt % mMAP-cAMP was dissolved in a solvent of distilled water:ethanol (30:70), and an $FeCl_3$ solution was added such that a molar ratio of $Fe^{3+}$:DOPA is 1:3. The mixed solution was then electrospun. The electrospinning was performed by applying a high voltage of 6 kV to 14 kV when passing through a needle having a diameter of 0.4 mm while discharging the solution at a flow rate of 1 mL/h using a syringe pump, thereby forming a nanoparticle. Thus-prepared nanoparticle was collected into a stirring water bath containing phosphate buffered saline (PBS; pH 7.4) or an aluminum foil. Compared to a conventional solution phase, the MAP-cAMP showed a reduced positive charge as it becomes a nanoparticle and showed a surface potential similar to a charge pattern of the nanoparticle of the control MAP (FIG. 8).

Accordingly, the nanoparticle based on the antimicrobial adhesive protein according to the present invention is present in an inactive form and dissolved at a time point where antimicrobial activity is required, thereby establishing technology enabling expression of the antimicrobial activity. In this regard, the nanoparticle can be used in killing of infected bacteria inside cells without affecting infected host animal cells.

(3) Preparation of Gentamicin-Loaded Antimicrobial Nanoparticle

To prepare an Fe(III)-DOPA nanoparticle loaded with gentamicin (GENT), a GENT solution was added to the mixed solution, and the mixed solution was directly electrospun into PBS. Dialysis was performed three times against the PBS (pH 7.4) using a molecular weight cut off (MWCO) 3500 membrane to remove unloaded GENTs, thereby obtaining a purple pure GENT-loaded Fe(III)-DOPA complex nanoparticle.

Figure 9:
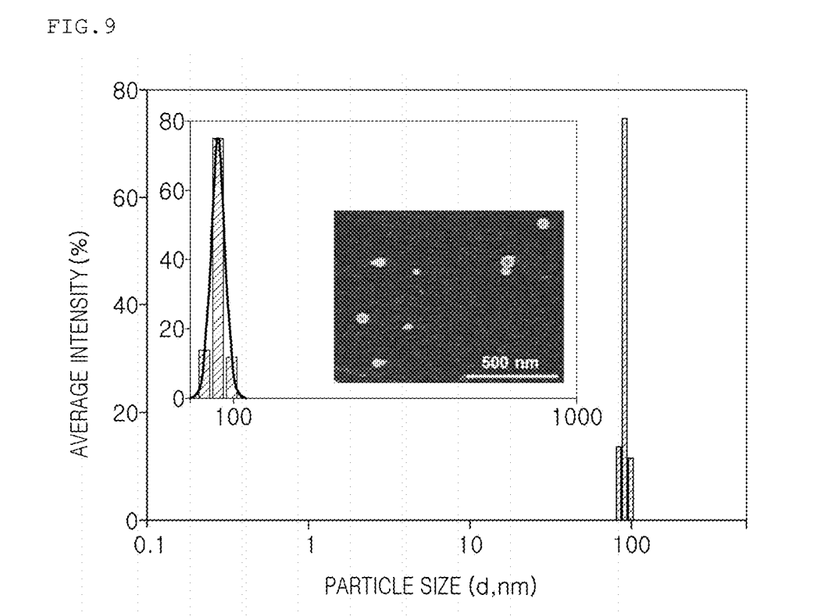
FIG. 9 illustrates results of SEM observation and particle size distribution of the antimicrobial nanoparticle MAP-cAMP-NPs.
Figure 10:
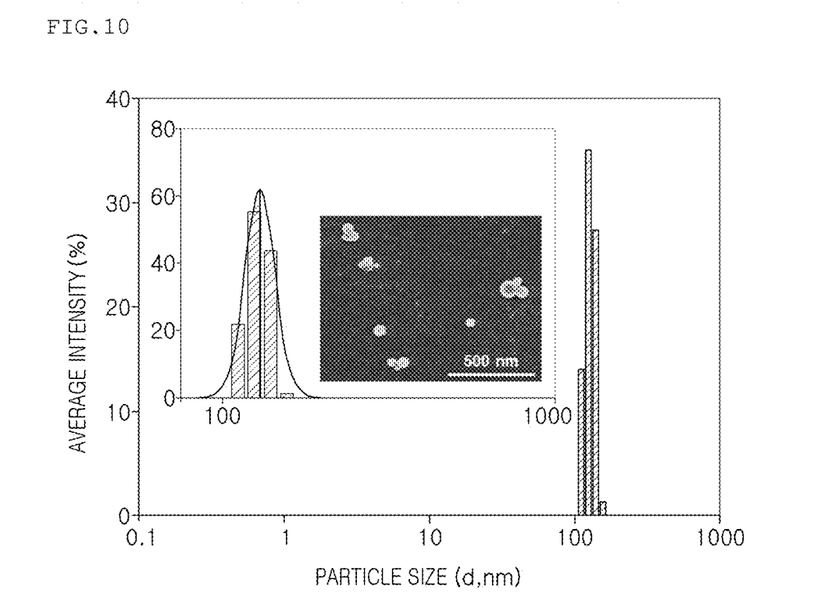
FIG. 10 illustrates results of SEM observation and particle size distribution of the antimicrobial nanoparticle loaded with gentamicin (MAP-cAMP@GENT)-NPs.

A DLS analysis showed that the MAP-cAMP-NP and (MAP-cAMP@GENT)-NP had average diameters of about 90 nm and about 135 nm, respectively (FIGS. 9 and 10).

4. Measurement of Antimicrobial Effect of Antimicrobial Nanoparticle (1) Measurement of Antimicrobial Effect of Antimicrobial Nanoparticle According to pH Condition To examine whether the MAP-cAMP-NP, the antimicrobial nanoparticle obtained in 3.(2), exhibits antimicrobial activity, the nanoparticle was applied to 500 μL of an LB liquid medium inoculated with 5 μL of $E.\ coli$, a gram-negative bacterium and cultured for 24 hours to measure optical density for 600 nm ($OD_{600}$). A 48-well culture plate was used for the culturing of the bacterial strain at 37° C. and 300 rpm.

Figure 11:
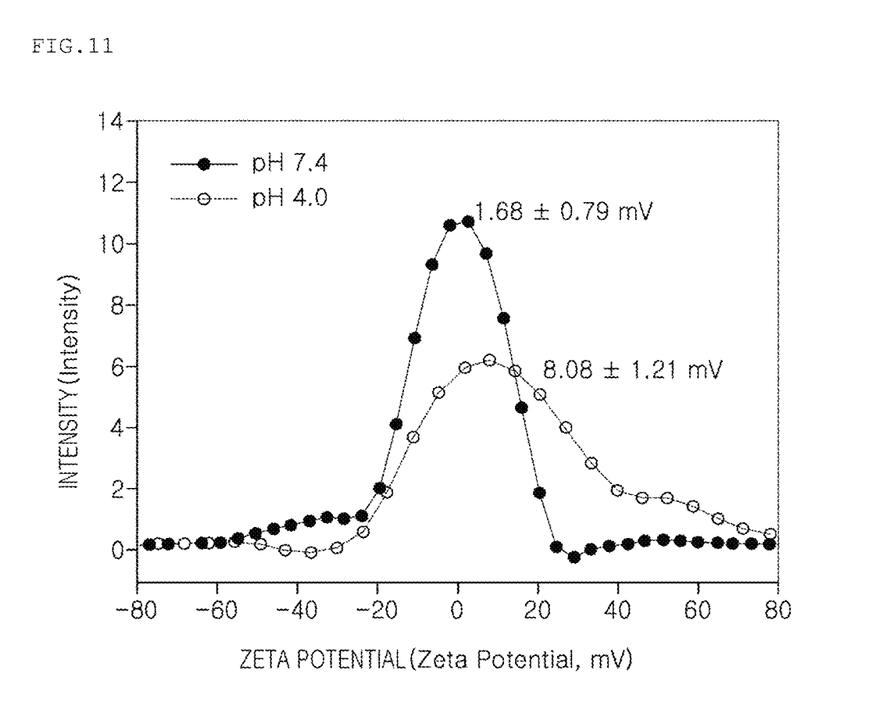
FIG. 11 illustrates a result of measuring charges of the antimicrobial nanoparticle MAP-cAMP-NPs in a neutral environment (pH 7.4) and an acidic environment (pH 4.0).
Figure 12:
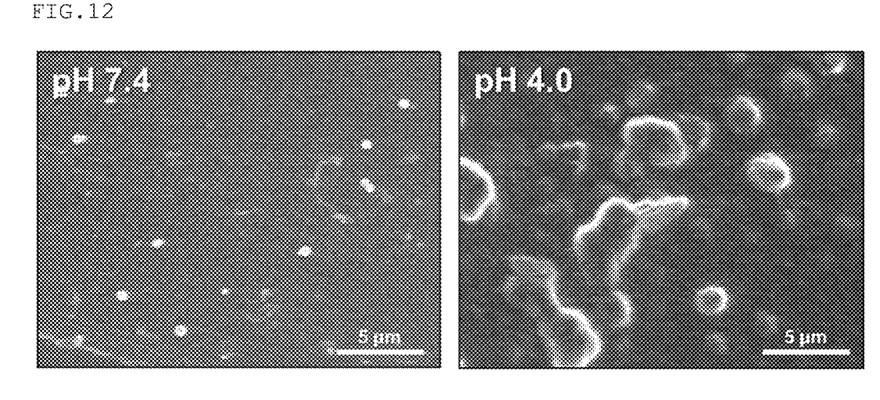
FIG. 12 illustrates results of SEM of the antimicrobial nanoparticle MAP-cAMP-NPs in a neutral environment (pH 7.4) and an acidic environment (pH 4.0).

As a result, the antimicrobial nanoparticle MAP-cAMP-NP was shown to exhibit a higher positive charge in a solution of pH 4.0, an acidic environment, than in a solution of pH 7.4, a neutral environment (FIG. 11). It can be seen that the positive charge of the nanoparticle, which was reduced while becoming a nanoparticle, is dissolved in an acidic environment, such as a bacterial infection environment, to restore an original positive charge. Further, SEM observation shows that the antimicrobial nanoparticle MAP-cAMP-NP exhibits a disintegration pattern of the existing nanoparticle form in an acidic environment (FIG. 12).

(2) Measurement of Antimicrobial Effect of Antimicrobial Nanoparticle in a Bacterial Infection Environment To measure the antimicrobial activity of the antimicrobial nanoparticle MAP-cAMP-NP obtained in 3.(2), the nanoparticle was applied to the liquid medium inoculated with bacteria at concentrations of 0 μg/mL, 0.25 μg/mL, 0.5 μg/mL, 1 μg/mL, 1.5 μg/mL and 2 μg/mL.

Specifically, the nanoparticle of each concentration was applied to 500 μL of an LB liquid medium inoculated with 5 μL (about 5×10$^5$ CFU) of gram negative $E.\ coli$ and cultured for 12 hours and 24 hours to measure optical density for 600 nm ($OD_{600}$). A 48-well culture plate was used for the culturing of the bacterial strain at 37° C. and 300 rpm.

Figure 13:
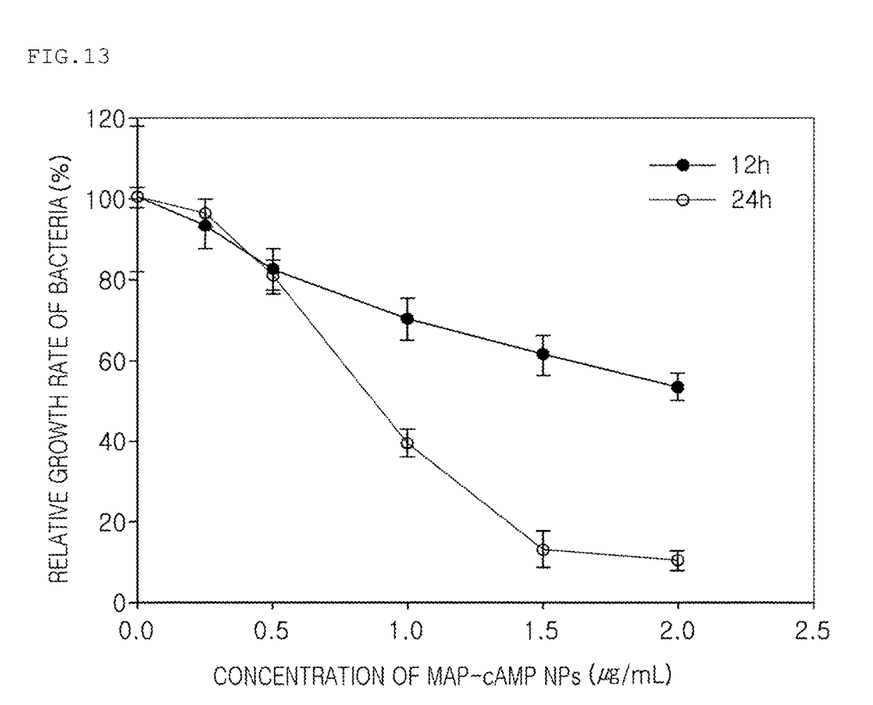
FIG. 13 is a graph illustrating optical density values 12 hours and 24 hours after applying various concentrations of the antimicrobial nanoparticle MAP-cAMP-NPs to the liquid culture medium in which *E. coli* is cultured.

As a result, a minimum coating concentration ($MIC_{90}$) of the MAP-cAMP-NP was shown to be 1.5 μg/mL for 90% inhibition of the growth of the $E.\ coli$ and that ($MIC_{50}$) was shown to be 1.0 mg/mL for 50% inhibition of the growth of the $E.\ coli$ (FIG. 13).

While embodiments have been shown and described in detail above, it will be apparent to those skilled in the art that modifications and variations could be made without departing from the scope of the present disclosure as defined by the appended claims.

---

The invention claimed is:

1. An antimicrobial composition comprising an antimicrobial nanoparticle having inherent antimicrobial activity in an amount of 1.0 μg/mL to 2 μg/mL, wherein the antimicrobial nanoparticle comprises an antimicrobial adhesive protein comprising an antibiotic peptide linked to a mussel adhesive protein derivative of which a tyrosine residue in the mussel adhesive protein is modified to a catechol derivative; and a metal capable of coordinating with the mussel adhesive protein derivative, wherein the antimicrobial nanoparticle has an antimicrobial effect under a bacterial infection environment condition of pH 0.1 to pH 6.5.

2. The antimicrobial composition of claim 1, wherein the catechol derivative is at least one selected from the group consisting of 3,4-dihydroxyphenylalanine (DOPA), DOPA o-quinone, dopamine, norepinephrine, epinephrine, epigallocatechin gallate and derivatives thereof.

3. The antimicrobial composition of claim 1, wherein the metal capable of coordinating with the mussel adhesive protein derivative is at least one selected from the group consisting of titanium, vanadium, chrome, manganese, iron, cobalt, nickel, zirconium, niobium, molybdenum, technetium, ruthenium, rhodium, palladium, silver, hafnium, tantalum, tungsten, rhenium, osmium, iridium, platinum and gold.

4. The antimicrobial composition of claim 1, wherein the antimicrobial adhesive protein is additionally loaded with an antimicrobial agent.

5. The antimicrobial composition of claim 4, wherein the antimicrobial agent is at least one selected from the group consisting of penicillins, cephalosporins, β-lactams, macrolides, glycopeptides, lincosamides, quinolones, rifamycin, chloramphenicol, polymyxin, trimethoprim, streptogramin, oxazolidinone, gentamicin and bacitracin.

6. The antimicrobial composition of claim 1, wherein the mussel adhesive protein is a protein selected from the group consisting of *Mytilus edulis* foot protein (Mefp)-1, Mefp-2, Mefp-3, Mefp-4, Mefp-5, *Mytilus galloprovincialis* foot protein (Mgfp)-1, Mgfp-2, Mgfp-3, Mgfp-4, Mgfp-5, *Mytilus coruscus* foot protein (Mcfp)-1, Mcfp-2, Mcfp-3, Mcfp-4, Mcfp-5, foot protein (fp)-1, fp-2, fp-3, fp-4, fp-5 and fp-6, a variant thereof, or a fusion protein to which at least one protein selected from the group is linked.

7. The antimicrobial composition of claim 1, wherein the antibiotic peptide is at least one peptide selected from the group consisting of an Annexin A7 peptide (A7 peptide) a Tet-20 peptide, a minTBP peptide and an MP196 peptide.

8. The antimicrobial composition of claim 1, wherein the antimicrobial composition has inherent antimicrobial activity without any additional antimicrobial agent.

* * * * *